United States Patent [19]

della Valle

[11] 4,452,811
[45] Jun. 5, 1984

[54] MONOHALOGENATED DERIVATIVES OF 7-HYDROXY-COUMARIN, PHARMACEUTICAL COMPOSITIONS CONTAINING THE SAME AND METHODS OF USING SAID COMPOSITIONS

[75] Inventor: Francesco della Valle, Padova, Italy

[73] Assignee: Fidia S.p.A., Abano Terme, Italy

[21] Appl. No.: 344,521

[22] Filed: Feb. 1, 1982

Related U.S. Application Data

[63] Continuation of Ser. No. 160,175, Jun. 17, 1980, abandoned, and a continuation-in-part of Ser. No. 952,460, Oct. 18, 1978, abandoned.

[30] Foreign Application Priority Data

Nov. 17, 1977 [IT] Italy .............................. 29765 A/77

[51] Int. Cl.$^3$ ..................... A61K 31/37; C07D 311/08
[52] U.S. Cl. ............................... 424/281; 424/248.55; 424/267; 544/151; 546/196; 549/289
[58] Field of Search .................... 544/151; 549/289; 546/196; 424/281, 248.55, 267

[56] References Cited

U.S. PATENT DOCUMENTS

| | | | |
|---|---|---|---|
| 3,259,635 | 7/1966 | Ritter et al. | 549/289 |
| 3,515,721 | 6/1970 | Ritter et al. | 549/289 |

FOREIGN PATENT DOCUMENTS

| | | | |
|---|---|---|---|
| 276377 | 11/1969 | Austria . | |
| 2039867 | 2/1972 | Fed. Rep. of Germany . | |
| 2108185 | 9/1972 | Fed. Rep. of Germany . | |
| 2530405 | 1/1977 | Fed. Rep. of Germany . | |
| 2543945 | 4/1977 | Fed. Rep. of Germany . | |
| 2361 | 2/1964 | France . | |
| 1044608 | 7/1965 | United Kingdom . | |
| 1146792 | 6/1967 | United Kingdom | 549/289 |
| 1362337 | 7/1972 | United Kingdom . | |
| 2008109A | 11/1978 | United Kingdom . | |
| 2008109B | 11/1978 | United Kingdom . | |

OTHER PUBLICATIONS

Chemical Abstract 68: 59434b.
Aporti et al., Chem. Abs. 89: 209049e, 1978.

*Primary Examiner*—Jane T. Fan
*Attorney, Agent, or Firm*—Birch, Stewart, Kolasch & Birch

[57] ABSTRACT

A selective process is described for producing monohalogenated derivatives of 7-hydroxy coumarin wherein the halo substituent is at the desired position and the final product is free of other monohalogenated isomers. The resulting products and pharmaceutical compositions containing the same, especially those wherein the halo substituent is at the 8 position, have valuable specific coronary vasodilating activity.

18 Claims, No Drawings

MONOHALOGENATED DERIVATIVES OF 7-HYDROXY-COUMARIN, PHARMACEUTICAL COMPOSITIONS CONTAINING THE SAME AND METHODS OF USING SAID COMPOSITIONS

CROSS REFERENCE TO RELATED APPLICATIONS

This application is a continuation of application Ser. No. 160,175 filed on June 17, 1980, abandoned which is a continuation-in-part application of Ser. No. 952,460 filed on Oct. 18, 1978 and now abandoned.

BACKGROUND OF THE INVENTION

1. Field of the Invention

The present invention relates to a selective process for the preparation of basic coumarin derivatives and salts thereof which are formed by the reaction with organic and inorganic salts. The basic coumarin derivatives are represented by the formula:

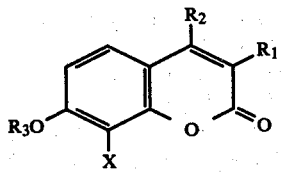

wherein $R_1$ is selected from alkyl groups having basic substituents thereon such as piperidino ethyl, morpholino ethyl, diethylamino ethyl or diethylamino propyl; $R_2$ is selected from the group consisting of hydrogen, alkyl and aryl groups; $R_3$ is selected from the group consisting of alkyl radicals substituted with a basic group, an alkenyl group, a carboxy alkyl group or an alkoxy carbonyl alkyl group; and wherein X represents a halogen atom in the 8 position.

The process according to the present invention makes it possible to obtain as final products monohalogenated derivatives of 7-hydroxycoumarin of the formula:

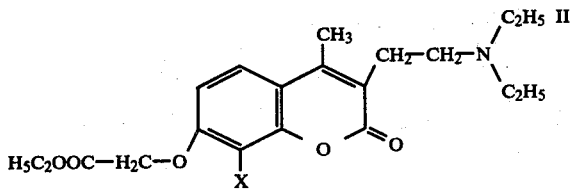

wherein X is as defined above. By virtue of the selective process which forms the compounds of the present invention in accordance with the objects of the present invention, it is certain that the halogen atoms are in position 8 in the final products. As will be shown hereinafter, the final products obtained in accordance with the present invention have a grade and purity sufficient to exercise a vasodilatory action effectively, in particular with respect to coronary vessels in animals and humans.

2. Prior Art

A pharmaceutical product under the generic name of "carbochromene" is already known which is represented by the general formula:

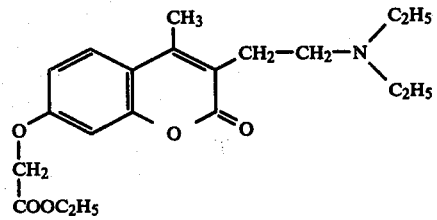

U.S. Pat. No. 3,515,721 discloses some mono- and di-halogen derivatives and method for forming the same which have the general formula:

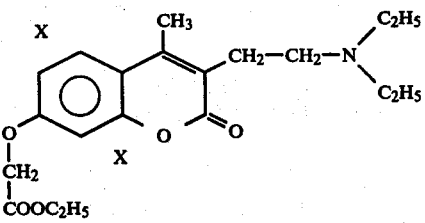

These compounds also possess specific coronary vasodilatory activity but to a lower degree (see compound Nos. 4 and 10 in the included table), according to data furnished in the patent, with respect to carbochromene (compound No. 2 of the table).

Furthermore, in the above-mentioned patent, it is stated that there is obtained, in the case of monohalogenated derivatives, a single final product and only in the corresponding British specification No. 1,146,792 is it specified that the halogen is in position 8.

However, such a product is in fact composed of a mixture of derivatives of 7-hydroxy-coumarin and there are also present therein compounds having a halogen atom in the position indicated by X, i.e., position 8 or position 6.

The uncertainty as where the halogen is located is a result of the procedure used to make the compounds. Since the halogen is introduced during an intermediate phase of the process, it is not possible to determine with certainty what position will the halogen occupy.

DESCRIPTION OF THE INVENTION

Surprisingly, according to the present invention, studies on the activity of mono-halogenated derivatives having the halogen atom in position 8, have revealed that such monohalogenated derivatives possess a vasodilatory activity in animals notably superior to that of carbochromene (compare compound No. 3 with compounds Nos. 6 and 9 in Table I) and which have a melting point different from those indicated in the above-mentioned prior patents as noted in Table I.

According to the present invention, the process of preparing the compounds of the invention comprises (a) reacting a 2-haloresorcinol compound of the formula:

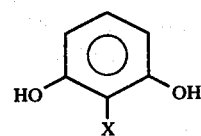

with a β-keto ester to obtain an intermediate compound of the formula:

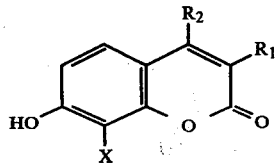

VI wherein $R_1$, $R_2$ and X are as indicated in formula I hereinabove; and (b) further reacting the intermediate compound VI with a compound of the formula $R_3$—X, wherein $R_3$ is as indicated in formula I, and X indicates a halogen atom such as Br-, Cl- or I-, for example, in the presence of an acid-binding agent to obtain the desired compound.

Another process also according to the present invention comprises reacting a mono-alkylated 2-halo-resorcinol compound of the formula:

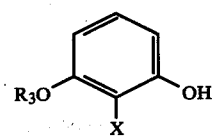

VII wherein $R_3$ and X are as indicated above, with β-keto ester to obtain the desired product.

The following examples are given for the purpose of illustrating the present invention. All temperatures are in degrees centigrade.

EXAMPLE 1

8-chloro-3-(β-diethylaminoethyl)-4-methyl-7-hydroxy-coumarin

To 50.6 g of 2-chloro-resorcinol (prepared according to N. Schamp. Bull, Soc. Chim. Belg., 73, 35 (1946): Hans Verner Wanzlick and Steffi Mohrmann, Chem. Ber., 96, 2257 (1963) there are added 80.2 g of the ethyl ester of α-(β-diethyl aminoethyl)acetoacetic acid and 66.5 g of p-toluene-sulfonic acid.

The mixture is slowly poured into 770 g of polyphosphoric acid while stirring. The temperature of the mixture should not exceed 35°.

After about 24 hours 1 kg of ice is added. A precipitate of the salt of 8-chloro-3(β-diethylaminoethyl)-4-methyl-7-hydroxy-coumarin is obtained and is separated by filtration.

The 8-chloro-3(β-diethylaminoethyl)-4-methyl-7-hydroxy-coumarin is freed with an aqueous solution of sodium carbonate.

Yield 70%, m.p. 220°.

The hydrochloride of the 8-chloro-3(β-diethylaminoethyl)-4-methyl-7-hydroxy-coumarin produced by the process melts at 246°-266°. The prior art (R. Beyerle and R. E. Nitz, British specification No. 1,146,792 page 4, lines 125-127) gives a melting point for the hydrochloride at 278°. The solid obtained by the cited authors (by chlorination of the 3(β-diethylaminoethyl)-4-methyl-7-hydroxy-coumarin) does not correspond to the hydrochloride of 8-chloro-3(β-diethylaminoethyl)-4-methyl-7-hydroxy-coumarin, but to a mixture containing various compounds, among which is the 6-chloro isomer.

In fact, the 6-chloro-3(β-diethylaminoethyl)-4-methyl-7-hydroxy-coumarin hydrochloride prepared according to the process of the invention, but starting with 4-chloro-resorcinol melts at 284°-287°.

The preparation described by R. Beyerle and R. E. Nitz was then repeated.

A simple thin layer of chromatographic analysis showed that the product produced consisted of a mixture of 6-chloro-3(β-diethylaminoethyl)-4-methyl-7-hydroxy-coumarin hydrochloride, 8-chloro-3(β-diethylaminoethyl)-4-methyl-7-hydroxy-coumarin hydrochloride and other compounds. (See table I (note)

EXAMPLE 2

8-chloro-3(β-diethylaminoethyl)-4-methyl-7-ethoxycarbonylmethoxy-coumarin 50 g of 8-monochloro-3(β-diethylaminoethyl)-4-methyl-7-hydroxy-coumarin are suspended in 600 ml of acetone; 70 g of potassium carbonate and 65 g of ethyl monochloroacetate are then added thereto and the mixture is refluxed for 14 hours.

After filtration, the solution is evaporated under reduced pressure and the residue is dissolved in dilute acetic acid (15 ml acetic acid in 400 ml water).

The aqueous solution is made basic with ammonia. A solid which after recrystallization from ethyl acetate gives the 8-chloro-3(β-diethylaminoethyl)-4-methyl-7-ethoxycarbonylmethoxy-coumarin, m.p. 147°-8° is obtained. The hydrochloride thereof melts at 219°-20°. The literature already cited in the first example gives, for the hydrochloride, a melting point of 88°. As it was indicated before, the solid obtained in the prior art corresponds to a mixture of compounds. (See table I (note)

EXAMPLE 3

8-bromo-3(β-diethylaminoethyl)-4-methyl-7-hydroxy-coumarin

To 14.2 g of 2-bromoresorcinol (prepared according to N. Schamp and H. DePooter, Bull. Soc. Chim. Belg., 75, 391, 1966) there are added 17.1 g of the ethyl ester of α(β-diethylaminoethyl)acetoacetic acid and 14 g of p-toluenesulfonic acid.

The mixture is slowly poured, with stirring, into 170 g of polyphosphoric acid. The temperature of the mixture should not exceed 35°.

After 24 hours 300 g of ice is added. The salt of 8-bromo-3(β-diethylaminoethyl)-4-methyl-7-hydroxy-coumarin which precipitates is collected by filtration.

The 8-bromo-3(β-diethylaminoethyl)-4-methyl-7-hydroxy-coumarin is freed with an aqueous solution of sodium carbonate.

Yield 80%, m.p. 250°.

The bromohydrate of 8-bromo-3(β-diethylaminoethyl)-4-methyl-7-hydroxy-coumarin melts at 325°.

British Pat. No. 1,146,792 to Beyerle and Nitz as well as other patents, give a melting point of 261° for the bromohydrate. The solid obtained by the prior art by bromination of 3(β-diethylaminoethyl)-4-methyl-7-hydroxy-coumarin is composed by a mixture of compounds.

EXAMPLE 4

8-bromo-3(β-diethylaminoethyl)-4-methyl-7-ethoxycarbonylmethoxy-coumarin 20 g of 8-bromo-3(β-diethylaminoethyl)-4-methyl-7-hydroxy-coumarin are suspended in 300 ml of acetone. 35 g of potassium carbonate and 25 g of ethyl monochloro-acetate are added thereto and the mixture is refluxed for 20 hours.

After filtration, the acetone filtrate is evaporated under reduced pressure and the residue is dissolved in dilute acetic acid. The aqueous solution is made basic with ammonia. A solid which, when recrystallized from ethyl acetate, gives the product, 8-bromo-3(β-diethylaminoethyl)-4-methyl-7-ethoxycarbonylmethoxy-coumarin, m.p. 150°–151° is thus obtained. The hydrochloride of this product melts at 200°–201°. The prior art cited in Example 1 gives a melting point of 177° for this hydrochloride.

Following the previous reasoning, the solid obtained by the prior art consisted of a mixture of compounds.

EXAMPLE 5

Mono-ethoxycarbonyl methyl-2-chloro-resorcinol 31. g of 2-chlororesorcinol are treated with 800 ml of acetone. 29 g of potassium carbonate and 26 g of ethyl chloracetate are added thereto. The suspension is then refluxed for 48 hours.

After filtration, the acetone filtrate is evaporated. The residue gives 29 g of mono-ethoxycarbonyl methyl-2-chlororesorcinol m.p. 75°–76°.

EXAMPLE 6

8-chloro-3(β-diethylaminoethyl)-4-methyl-7-ethoxycarbonyl methoxy coumarin (starting with monoethoxycarbonyl methyl 2-chloro-resorcinol)

To 15 g of monoethoxycarbonyl methyl 2-chlororesorcinol there are added 15 g of the ethyl ester of α(β-diethylaminoethyl) acetoacetic acid and 12 g of p-toluenesulfonic acid.

The mixture is poured slowly, with stirring, in 200 g of polyphosphoric acid. The temperature should not exceed 35°.

After 24 hours the mixture is treated as in Example 2. There is obtained a crystalline material, m.p. 147°–148°.

EXAMPLE 7

Evidence of Utility in increasing coronary flux of Mammals: Experimental Conditions and Method for Measuring coronary Vasodilator Activity These studies were effected on dogs having a weight between 18 and 30 kg. The action of the compound was examined under anaesthesia immediately after surgery. The anaesthesia was induced with sodium thiopentone (15 mg/kg, e.v.) and maintained with chloralose (80–100 mg/kg, e.v.). Supplementary doses of chloralose were given during the experiment to keep the anaesthesia constant.

The animals were subjected to intermittent positive pressure ventilation. The preparation for surgery consisted in the installation of the following devices: electromagnetic flux transductor and a plastic probe (to mechanically zero the flux indicator in case of a temporary arrest of the blood flow) on the left circumflexed coronary artery which had been prepared through left toroacothomy; an electromagnetic flux transductor and a probe in the femoral artery; a catheter in the other femoral artery to record the arterial pressure; a catheter in the femoral vein adjoining the catheterized femoral artery, or in the external jugular vein, for the injection of the test materials; a catheter in the left ventricle through a common carotid to record the ventricular pressure and its first derivative (dp/dt); a catheter in the coronary sinuses (two dogs) for the withdrawal of venous blood in the left coronaries; a thin hypodermic needle (246) connected to a catheter in the left circumflexed coronary artery for the intracoronary injection of the test substances. The oxygen content in the coronary sinuses was measured with a Van Slyke apparatus.

The studies have been performed on the dogs 4–6 days after the installation of an electromagnetic flux transducer on the ascending aorta, a catheter in the ascending aorta to register the blood pressure and a catheter in the external jugular vein for endovenous injections.

This surgical preparation was performed under anaesthesia with sodium pentathol (30 mg/kg) under sterile conditions. During the experiment the animals are allowed to remain quiet on a padded bed, without sedatives and without restraining means. They were used to measure the cardiac output, left ventricular work per minute (cardiac throw for mean aortic pressure) length of the sistule (ejection phase) and the first derivative of the curve of aortic flux (df/dt) together with the blood pressure and cardiac frequency.

To measure the blood flow and blood pressure there were used respectively Biotronex No. 610 amplifiers and Battaglia Rangoni No. 1 1A transductors.

The data have been visually observed on a Hewlett Packard 4588 optical recorder. The vascular resistances for the coronary and femoral lumens have been calculated as the relationship between the mean arterial pressure in mm Hg and the blood flow in ml/min. The intracoronary and endovenous administration of the test substances was performed in a period of 20–30 seconds. The test substances were diluted in physiological solution (0.5 ml/kg).

The results obtained are set forth in the following Table I.

TABLE I

| | Comparative Tests Showing Vasodilator Activity | | | | | |
|---|---|---|---|---|---|---|
| Substance | Dosage i.v. | Maximum Increase in Coronary Flux (Percent) | Length of action (minutes) | Change in Blood Pressure (Percent) | m.p. p.f. (°C.) | Pharmacological data from |
| (1) Papaverine | 0.8 | 23–24 | 8–10 | −20 | | U.S. Pat. No. 3,515,721 No. 3,259,635 |
| (2) 3(β-diethylamino ethyl)-4-methyl-7-ethoxy carbonyl methoxy coumarin hydrochloride (carbochromene) | 2.8 | 67 | 75 | −4 | 159–160° C. | U.S. Pat. No. 3,259,635 |
| (3) Same as under (2) | 2.0 | 104 | 65 | −2 | 159–160° C. | our experimental data |

TABLE I-continued

Comparative Tests Showing Vasodilator Activity

| Substance | Dosage i.v. | Maximum Increase in Coronary Flux (Percent) | Length of action (minutes) | Change in Blood Pressure (Percent) | m.p. p.f. (°C.) | Pharmacological data from |
|---|---|---|---|---|---|---|
| (4) Product (1) described in example 3 of U.S. Pat. No. 3,515,721 | 2.0 | 38 | 40 | — | 188° C. | U.S. Pat. No. 3,515,721 |
| (5) Product (1) prepared by us following example no. 3 of U.S. Pat. No. 3,515,721 | 2.0 | 42 | 45 | — | 187–255° C. | our experimental |
| (6) 8-monochloro-3($\beta$ diethylamino ethyl)-4-methyl-7-ethoxy carbonylmethoxy coumarin hydrochloride | 2.0 | 272 | 85 | ±0 | 219–220° C. | our experimental data - example 2 |
| (7) 6-monochloro-3($\beta$ diethylamino ethyl)-4-methyl-7-ethoxy carbonylmethoxy coumarin hydrochloride | 2.0 | 70 | 50 | ±0 | 213° C. | our experimental data |
| (8) 5-monochloro-3($\beta$-diethylamino ethyl)-4-methyl-7-ethoxy carbonyl methoxy coumarin hydrochloride | 2.0 | 30 | 20 | ±0 | 150° C. | our experimental data |
| (9) 6-monobromo-3($\beta$-diethylamino ethyl)-4-methyl-7-ethoxy carbonyl methoxy coumarin hydrochloride | 2.0 | 210 | 70 | ±0 | 202–203° C. | our experimental data - example 4 |
| (10) -monobromo-3($\beta$-diethylamino ethyl-4-methyl-7-ethoxy carbonyl methoxy coumarin hydrochloride | 2.0 | 37 | 30 | — | 177° C. | U.S. Pat. No. 3,515,721 |

(1) In reality it is the question of not a sole compound, but a mixture of compounds.

NOTE: Example 3 of U.S. Pat. No. 3,515,721 has been repeated several times. The chloridation reaction (III paragraph, Example 3) was repeated several times.

The results concerning the yield correspond to what is described in the patent.

It is to be noted that the solid obtained is clearly a mixture formed by several compounds, among which it is possible to recognize 6-monochloro-3-$\beta$-diethylaminoethyl-4-methyl-7-hydroxy coumarin hydrochloride (chromatography on a thin layer using as eluent chloroform, methanol, ammonia 2 N (containing 3% of ammonium acetate) 80:20:2).

By quantitative determination it was ascertained that in the final solid that in 8-monochloro-3-$\beta$-diethylaminoethyl-4-methyl-7-hydroxy coumarin hydrochloride is present in an amount of only 18%.

The alkylation reaction (I paragraph, Example 3) was repeated several times.

The results concerning the yield correspond to what is described in the patent.

It is to be noted that the solid obtained is clearly a mixture formed by several compounds among which it is possible to recognize 6-monochloro-3-$\beta$-diethylaminoethyl-4-methyl-7-ethoxycarbonylmethoxy coumarin hydrochloride (chromatography on a thin layer using cycloexane-diethylamine-acetone 80:10:10).

By quantitative determination it was ascertained that the final solid that 8-monochloro-3-$\beta$-diethylaminoethyl-4-methyl-7-ethoxycarbonylmethoxy coumarin hydro-chloride is present in an amount of only 30%.

The above-described compounds of the present invention and their pharmaceutically salts, such as the hydrochloride salts can be therapeutically utilized orally as well as by injection. Oral compounds can be administered in different forms such as in the form of dragees, tablets, gelatin capsules as well as in other known forms and can be formulated in a manner well known to pharmaceutical chemists utilizing standard pharmaceutical excipients, carriers or diluents such as water, vegetable oils, syrup, gum arabic, gelatin, methylcellulose, polyglycols and others which may optionally be mixed with emulsifying agents. The compounds of the present invention and the pharmaceutically acceptable salts thereof such as the hydrochloride salt may be injected intramuscularly or endovenously in the form of an injectable solution. The pharmaceutical preparations can be liquid or dried, for example lyophilized preparations, using suitable excipients or diluents which are well known to pharmaceutical chemists. Useful oral dosages are in the range of about 50–400 mg or active ingredient daily. Useful injection doses are in the range of about 20–100 mg daily for intramuscular or intravenous injection.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A substantially pure compound having the formula:

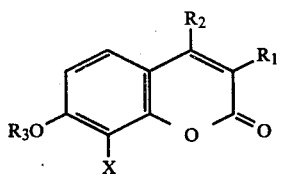

wherein X represents a halogen atom, $R_1$ is selected from the group consisting of piperidino ethyl, morpholino ethyl, diethylamino ethyl and diethylamine propyl, $R_2$ is selected from the group consisting of methyl and phenyl, and $R_3$ is selected from the group consisting of ethoxycarbonyl methyl and ethoxycarbonyl ethyl or a pharmaceutically acceptable salt thereof.

2. The substantially pure compound according to claim 1, wherein X is selected from the group consisting of Br, Cl or I.

3. The substantially pure compound according to claim 1, 8-monochloro-3(β-diethylaminoethyl)-4-methyl-7-ethoxycarbonylmethoxy coumarin or a pharmaceutically acceptable salt thereof.

4. The substantially pure compound according to claim 1, 8-monobromo-3(β-diethylaminoethyl)-4-methyl-7-ethoxycarbonylmethoxy coumarin or a pharmaceutically acceptable salt thereof.

5. The substantially pure compound according to claim 1, 8-monochloro-3(β-diethylaminoethyl)-4-methyl-7-ethoxycarbonylmethoxy coumarin hydrochloride, which melts at about 219°–220° C.

6. The substantially pure compound according to claim 1, 8-monobromo-3(β-diethylaminoethyl)-4-methyl-7-ethoxycarbonylmethoxy coumarin hydrochloride, which melts at about 202°–203° C.

7. A pharmaceutical composition comprising an effective vasodilating amount of a substantially pure 7-hydroxycoumarin compound of the formula:

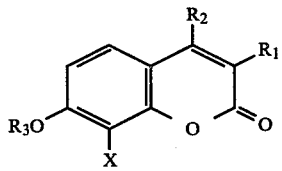

wherein X represents a halogen atom, $R_1$ is selected from the group consisting of piperidino ethyl, morpholino ethyl, diethylamino ethyl and diethylamino propyl, $R_2$ is selected from the group consisting of methyl and phenyl, and $R_3$ is selected from the group consisting of ethoxycarbonyl methyl and ethoxycarbonyl ethyl or a pharmaceutically acceptable salt thereof, and a pharmaceutically acceptable carrier or diluent.

8. The pharmaceutical composition according to claim 7, in the form of a tablet.

9. The pharmaceutical composition according to claim 7, in the form of a dragee.

10. The pharmaceutical composition according to claim 7, in the form of a capsule.

11. The pharmaceutical composition according to claim 7, in the form of an injectable solution.

12. A method of treating coronary diseases in mammals caused by the obstruction of blood vessels which comprises administering thereto an effective vasodilating amount of a substantially pure compound having the formula:

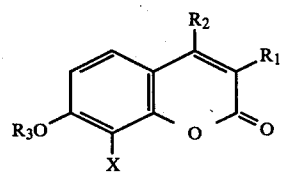

wherein X represents a halogen atom, $R_1$ is selected from the group consisting of piperidino ethyl, morpholino ethyl, diethylamino ethyl and diethylamino propyl, $R_2$ is selected from the group consisting of methyl and phenyl, and $R_3$ is selected from the group consisting of ethoxycarbonyl methyl and ethoxycarbonyl ethyl or a pharmaceutically acceptable salt thereof.

13. The method according to claim 12, wherein the active ingredient is administered orally to the human or animal in an amount of about 50–400 mg daily.

14. The method according to claim 12, wherein the active ingredient is administered intramuscularly or intravenously in an amount of about 20–100 mg daily.

15. The method according to claim 12, wherein said mammals are animals.

16. The method according to claim 12, wherein said mammals are canine.

17. The method according to claim 12, wherein said mammals are human.

18. The method according to claim 12, wherein said substantially pure compound is administered in an amount sufficient to effectively increase the coronary flux or said mammals.

* * * * *